(12) United States Patent
Verhalen (10) Patent No.: US 10,466,263 B2
(45) Date of Patent: Nov. 5, 2019

(54) PIPETTING DEVICE HAVING TWO TEMPERATURE SENSORS

(71) Applicant: Siemens Healthcare Diagnostics Products GmbH, Marburg (DE)

(72) Inventor: Christian Verhalen, Wiesbaden (DE)

(73) Assignee: Siemens Healthcare Diagnostics Products Gmbh, Marburg (DE)

( * ) Notice: Subject to any disclaimer, the term of this patent is extended or adjusted under 35 U.S.C. 154(b) by 213 days.

(21) Appl. No.: 15/230,175

(22) Filed: Aug. 5, 2016

(65) Prior Publication Data

US 2017/0045544 A1 Feb. 16, 2017

(30) Foreign Application Priority Data

Aug. 11, 2015 (EP) .................................... 15180477

(51) Int. Cl.
*G01N 35/10* (2006.01)
*B01L 3/02* (2006.01)
*G01N 35/00* (2006.01)

(52) U.S. Cl.
CPC .......... *G01N 35/1009* (2013.01); *B01L 3/021* (2013.01); *G01N 35/0099* (2013.01); *G01N 35/00594* (2013.01); *G01N 35/10* (2013.01); *B01L 2200/14* (2013.01); *B01L 2300/0627* (2013.01); *B01L 2300/0832* (2013.01); *B01L 2300/1805* (2013.01); *B01L 2300/1888* (2013.01); *G01N 2035/00425* (2013.01)

(58) Field of Classification Search
None
See application file for complete search history.

(56) References Cited

U.S. PATENT DOCUMENTS

| 5,856,194 A | * | 1/1999 | Arnquist | G01N 35/0092 422/63 |
| 2001/0017060 A1 | | 8/2001 | Offen et al. | |
| 2011/0163083 A1 | * | 7/2011 | Lin | F24H 9/2014 219/494 |
| 2013/0195718 A1 | * | 8/2013 | Michels | B01L 3/021 422/63 |

FOREIGN PATENT DOCUMENTS

| EP | 0 496 962 A2 | 8/1992 |
| EP | 1134024 A2 | 9/2001 |
| EP | 2 623 202 A1 | 8/2013 |
| WO | WO 97/02893 A1 | 1/1997 |

OTHER PUBLICATIONS

European Search Report of European Application No. 15180477.0-1553 dated Feb. 12, 2016.

* cited by examiner

*Primary Examiner* — Xiaoyun R Xu
(74) *Attorney, Agent, or Firm* — Dugan & Dugan, PC (57) ABSTRACT

The invention is in the field of automatic analysis devices and relates to a heatable pipetting device for an automatic analysis device and a method for providing a reaction mixture. The pipetting device comprises a pipetting needle having two temperature sensors at different distances to the tip of the pipetting needle.

5 Claims, 4 Drawing Sheets

PIPETTING DEVICE HAVING TWO TEMPERATURE SENSORS

CROSS REFERENCE TO RELATED APPLICATION

This claims priority to European Patent Application No. EP 15180477.0, filed Aug. 11, 2015, which is hereby incorporated by reference herein in its entirety for all purposes.

FIELD

The invention is in the field of automatic analysis devices and relates to a heatable pipetting device for an automatic analysis device and a method for providing a reaction mixture of a liquid to be analyzed and at least one reagent liquid, with the aid of the pipetting device.

BACKGROUND

Current analysis devices, as they are routinely used in analytics, forensics, microbiology, and clinical diagnostics, are capable of carrying out a variety of detection reactions and analyses using a variety of samples. To be able to carry out a variety of studies automatically, diverse automatically operating devices for the spatial transfer of measurement cells, reaction containers, and reagent liquid containers, for example, transfer arms having gripping function, transport belts, or rotatable transport wheels, as well as devices for the transfer of liquids, for example, pipetting devices, are housed in a device housing. The devices comprise a central control unit, which is capable, by means of corresponding software, of substantially independently planning and executing the work steps for the desired analysis.

Many analysis methods used in such automatically operating analysis devices are based on optical methods. Measurement systems which are based on photometric (for example, turbidimetric, nephelometric, fluorometric, or luminometric) or radiometric measurement principles are particularly widespread. These methods enable the qualitative and quantitative detection of analytes in liquid samples, without having to provide additional separation steps. The determination of clinically relevant parameters, for example, the concentration or the activity of an analyte, is often performed in that an aliquot of a bodily fluid of a patient is mixed simultaneously or successively with one or more test reagents in a reaction vessel to form a reaction mixture, whereby a biochemical reaction is started, which causes a measurable change of an optical property of the reaction mixture.

The measurement result is in turn relayed by the measurement system into a storage unit and analyzed. Subsequently, the analysis device supplies a user with sample-specific measured values via an output medium, for example, a monitor, a printer, or a network connection.

Numerous biochemical reactions for the detection of analytes have the optimum thereof in a temperature range from approximately 25 to 37° C., i.e., above a typical room temperature. It is therefore necessary to set and maintain the temperature of the reaction mixtures accordingly. This is known to be performed with the aid of heatable pipetting needles, in which an aspirated liquid volume is heated, so that upon dispensing of the liquid volume into a reaction vessel, the desired temperature is achieved in the reaction mixture to be provided. The use of heatable pipetting needles is in particular also necessary therefore because the reagent liquids and sometimes also the sample liquids in most analysis devices are cooled to temperatures of approximately 4 to 10° C., to increase the storage stability.

Heatable pipetting needles and the use thereof for providing temperature-controlled reaction mixtures are well known in the prior art.

Conventional pipetting needles are typically equipped with a heating device, a temperature sensor, and a controller for the heating device. The temperature sensor measures the current temperature of the pipetting needle and compares it to a predefined target temperature, for example, 38° C., or a predefined target temperature range. If it is determined, for example, that the current temperature is below the predefined target temperature, the heating device is activated via the controller until the target temperature is reached. Such a pipetting device is described, for example, in EP-A2-1134024.

Nonetheless, there are numerous technical requirements with respect to the heating of liquids in a pipetting needle, which require special adaptations. For example, it is problematic to ensure that different volumes can also be brought reliably to the desired dispensing temperature. A pipetting needle is proposed in EP-A2-0496962 for solving this problem, which has two independently operating heating devices, which are each equipped with a temperature sensor and with a controller.

In the present methods for providing a reaction mixture, in which a heatable pipetting needle is used, however, it is problematic that in spite of monitoring and regulation of the pipetting needle temperature, liquid volumes are pipetted again and again, which do not have the desired dispensing temperature, because typically an error message is only relayed to the control unit of the analysis device when it is determined that the pipetting needle temperature does not have the predefined target temperature over a longer period of time or over a plurality of pipetting procedures, and only then is a termination of all running analyses performed. Fundamentally, only a total failure of the temperature control function is thus recognized; individual pipetting procedures deviating from the target temperature are not recognized at all.

This has the disadvantage that in individual cases, reaction mixtures are provided, which do not have the required reaction temperature, which can result in a flawed measurement result. It is furthermore disadvantageous that in the event of a total failure of the temperature control function, all running analyses have to be terminated and then restarted, so that valuable sample and reagent liquids are lost to a large extent.

SUMMARY

The present invention is therefore based on the object of providing means and methods for an automatic analysis device, which cause a reduction of the risk of flawed measurement results as a result of temperature deviations in the reaction mixtures and which enable resource-conserving termination of further analyses if a total failure of the temperature-control function of a pipetting needle occurs.

This object is essentially achieved by the provision of a pipetting device according to the invention and the use thereof according to the invention. A pipetting device according to the invention is distinguished in that the pipetting needle is equipped with a first temperature sensor at a small distance from the tip of the pipetting needle and a second temperature sensor at a greater distance from the tip of the pipetting needle, wherein the second temperature sensor, which is more remote from the needle tip, does not have a connection per se to a controller for a heating device and is only used to measure a reference temperature value.

The subject matter of the present invention is therefore a pipetting device comprising:
- a pipetting needle having a tip and having a first temperature sensor at a small distance from the tip of the pipetting needle and a second temperature sensor at a greater distance from the tip of the pipetting needle,
- a heating device for the pipetting needle, and
- a controller for the heating device, wherein the first temperature sensor is connected to the controller for the heating device and the second temperature sensor has no connection to a controller for a heating device.

A pipetting needle is a hollow needle, for example, made of stainless steel, having a longitudinal axis, wherein the end of the hollow needle which is provided for receiving and dispensing a liquid to be transferred is designated as the tip. Proceeding from the tip, firstly a first temperature sensor is attached at a small distance from the tip of the pipetting needle and then a second temperature sensor is attached at a greater distance from the tip of the pipetting needle along the longitudinal axis of the pipetting needle of the pipetting device according to the invention. Only the first temperature sensor is connected to the controller for the heating device.

The term "controller for a heating device" is to be understood as a controller which can receive and process temperature measured values acquired by a temperature sensor and thereupon regulates the activity of the heating device.

The pipetting device according to the invention is preferably fastened on an automatically movable or pivotable transfer arm, which is part of an automatic analysis device. The pipetting device can therefore be moved horizontally between at least one liquid removal position and at least one liquid dispensing position. Furthermore, the pipetting device, or at least the pipetting needle, is movable in the vertical direction. At a liquid removal position, the pipetting needle is moved vertically downward, as much as possible along the center axis of the liquid vessel, until the needle tip plunges into the liquid. The plunging is registered with the aid of a corresponding sensor. By generating a partial vacuum in the pipetting needle by means of a metering pump, a defined volume of the liquid is aspirated, the pipetting needle is moved vertically upward and subsequently horizontally to the liquid dispensing position. At the liquid dispensing position, a defined liquid quantity is then dispensed into a target vessel, for example, a reaction vessel.

A further subject matter of the present invention is the use of a pipetting device according to the invention in a method for providing a reaction mixture of a liquid to be analyzed and at least one reagent liquid in a reaction vessel. The method comprises the following steps:
- aspirating a volume of a reagent liquid into the heated pipetting needle;
- moving the pipetting needle to the desired location of the dispensing of the aspirated volume of the reagent liquid into a reaction vessel; then
- measuring the temperature using the first and using the second temperature sensor;
- comparing the temperature measured by the first temperature sensor to a predefined minimum temperature and a predefined maximum temperature; and
- establishing that the temperature measured by the first temperature sensor either:
  - (i) exceeds the predefined maximum temperature, or
  - (ii) does not exceed the predefined maximum temperature and does not fall below the predefined minimum temperature, or
  - (iii) falls below the predefined minimum wherein
if it is established that the temperature measured by the first temperature sensor (i) exceeds the predefined maximum temperature or (iii) falls below the predefined minimum temperature—the aspirated volume of the reagent liquid is dispensed from the pipetting needle and then disposed of.

In the method according to the invention, in contrast to the methods from the prior art, the temperature of the pipetting needle is measured intentionally before each dispensing of a liquid volume and it is checked whether the measured temperature lies within a target value range. If the check has the result that the measured temperature lies outside the target value range, it is ensured that no reaction mixture is provided using the presumably incorrectly temperature-controlled liquid volume, contained in the pipetting needle, which is used at the end for ascertaining a measurement result. Instead, it is ensured that the presumably incorrectly temperature-controlled liquid volume is disposed of, i.e., discarded. This has the advantage that the risk of a faulty measurement result as a result of a temperature deviation in the reaction mixture is substantially reduced.

To carry out the method according to the invention, it is not absolutely necessary for a pipetting device according to the invention to be used, having a pipetting needle which has a first and a second temperature sensor, wherein only the first temperature sensor close to the needle tip is connected to the controller for the heating device. It is of course also possible to use a pipetting device having a pipetting needle which has a first and a second temperature sensor, wherein the first temperature sensor close to the needle tip and also the second temperature sensor remote from the needle tip are connected to a controller for the heating device(s), as long as a corresponding control of the method steps is ensured.

In one preferred embodiment of the method according to the invention, it is provided that—if it is established that the temperature measured by the first temperature sensor (ii) does not exceed the predefined maximum temperature and does not fall below the predefined minimum temperature—the following method steps are executed:
- ascertaining the absolute temperature difference between the temperature measured by the first temperature sensor and the temperature measured by the second temperature sensor;
- comparing the ascertained temperature difference to a predefined maximum temperature difference value; and
- establishing that the ascertained temperature difference is either
  - (a) greater than the predefined maximum temperature difference value or
  - (b) less than or equal to the predefined maximum temperature difference value, wherein
if it is established that (a) the ascertained temperature difference is greater than the predefined maximum temperature difference value—the aspirated volume of the reagent liquid is dispensed from the pipetting needle and then disposed of.

If the check has the result that the temperature measured by the first temperature sensor does lie within the predefined tolerance range, but the ascertained temperature difference is greater than the predefined maximum temperature difference value, it is ensured that no reaction mixture is provided using the presumably incorrectly temperature-controlled liquid volume, contained in the pipetting needle, which is used at the end for the ascertainment of a measurement result. Instead, it is ensured that the presumably incorrectly temperature-controlled liquid volume is disposed of, i.e., discarded. This has the advantage that the risk of a faulty measurement result as a result of a temperature deviation in the reaction mixture is reduced still further.

The disposal of an aspirated volume of reagent liquid can be performed in different manners. The disposal can be performed, for example, in that the pipetting needle is moved into a position in which the dispensing of the aspirated volume of the reagent liquid takes place into a waste vessel. In automatic analysis devices, which have washing stations for pipetting needles, the disposal can also be performed in that the pipetting needle is moved into a position in which the dispensing of the aspirated volume of the reagent liquid takes place into a washing station for pipetting needles. This has the advantage that a separate waste vessel does not have to be provided, and the disposal of the presumably incorrectly temperature-controlled liquid and the cleaning of the pipetting needle can be carried out in a single work step. Alternatively, it can also be provided that the aspirated volume of the reagent liquid is dispensed from the pipetting needle into the provided reaction vessel in spite of its presumably incorrect temperature, and the reaction vessel having the reaction mixture is then discarded.

In a further preferred embodiment of the method according to the invention, it is provided that—if it is established that the temperature measured by the first temperature sensor (ii) does not exceed the predefined maximum temperature and does not fall below the predefined minimum temperature—the following method steps are executed:
  ascertaining the absolute temperature difference between the temperature measured by the first temperature sensor and the temperature measured by the second temperature sensor;
  comparing the ascertained temperature difference to a predefined maximum temperature difference value; and
  establishing that the ascertained temperature difference is either
  (a) greater than the predefined maximum temperature difference value or
  (b) less than or equal to the predefined maximum temperature difference value,
  wherein
  if it is established that (b) the ascertained temperature difference is less than or equal to the predefined maximum temperature difference value—the aspirated volume of the reagent liquid is dispensed from the pipetting needle into the reaction vessel and the reaction vessel having the reaction mixture is supplied to a measurement unit, in which a physical property of the reaction mixture is measured.

The maximum temperature and the minimum temperature, which fundamentally define the temperature tolerance range, and the maximum temperature difference value are system-dependent variables, which have to be empirically ascertained in test series. System-dependent influencing factors are, for example, length, diameter, and material composition of the pipetting needle, the size of the reagent liquid volumes to be pipetted, the original absolute temperature of the reagent liquid, the original absolute temperature of the sample liquid, the absolute temperature which is to be achieved in the reaction mixture, etc. For a given analysis system, a test series is therefore to be carried out to establish maximum temperature, minimum temperature, and maximum temperature difference value, using which a suitable value is ascertained for the respective variable.

A further subject matter of the present invention is an automatic analysis device having at least one pipetting device according to the invention, as described above, which is fastened on an automatically movable or pivotable transfer arm.

One preferred embodiment of the automatic analysis device according to the invention furthermore comprises multiple receptacle positions for receiving reagent vessels, multiple receptacle positions for receiving reaction vessels, at least one measurement unit for measuring a physical property of a reaction mixture, and a controller, which is configured so that it controls a method according to the invention for providing a reaction mixture.

In particular, the controller is configured so that it controls a method for providing a reaction mixture of a liquid to be analyzed and at least one reagent liquid in a reaction vessel, having the following steps:
  heating the pipetting needle of the pipetting device;
  aspirating a volume of a reagent liquid into the heated pipetting needle;
  moving the pipetting needle to the desired location of the dispensing of the aspirated volume of the reagent liquid into a reaction vessel; then
  measuring the temperature using the first and using the second temperature sensor;
  comparing the temperature measured by the first temperature sensor to a predefined minimum temperature and a predefined maximum temperature; and
  establishing that the temperature measured by the first temperature sensor either:
  (i) exceeds the predefined maximum temperature, or
  (ii) does not exceed the predefined maximum temperature and does not fall below the predefined minimum temperature, or
  (iii) falls below the predefined minimum temperature,
  wherein
  if it is established that the temperature measured by the first temperature sensor (i) exceeds the predefined maximum temperature or (iii) falls below the predefined minimum temperature—the aspirated volume of the reagent liquid is dispensed from the pipetting needle and then disposed of.

In one preferred embodiment, the automatic analysis device comprises a controller, which is furthermore configured so that—if it is established that the temperature measured by the first temperature sensor (ii) does not exceed the predefined maximum temperature and does not fall below the predefined minimum temperature—the following method steps are additionally executed:
  ascertaining the absolute temperature difference between the temperature measured by the first temperature sensor and the temperature measured by the second temperature sensor;
  comparing the ascertained temperature difference to a predefined maximum temperature difference value; and
  establishing that the ascertained temperature difference is either
  (a) greater than the predefined maximum temperature difference value or
  (b) less than or equal to the predefined maximum temperature difference value,
  wherein
  if it is established that (a) the ascertained temperature difference is greater than the predefined maximum temperature difference value—the aspirated volume of the reagent liquid is dispensed from the pipetting needle and then disposed of.

A preferred automatic analysis device can have a receptacle position for a waste vessel and/or a washing station for pipetting needles. The disposal of an aspirated volume of the reaction liquid can then be performed in that the pipetting needle is moved into a position, in which the dispensing of the aspirated volume of the reagent liquid takes place into the waste vessel or into the washing station.

In one preferred embodiment, the automatic analysis device comprises a controller, which is furthermore configured so that—if it is established that a disposal of aspirated reagent liquid was performed in each of at least three successive pipetting procedures using the method according to the invention—the following method steps are additionally executed:

generating an error message and/or shutting down the pipetting device.

The controller is preferably configured so that the error message is displayed in the form of a text message or in the form of a pictogram on a display screen of the automatic analysis device or is emitted in the form of an acoustic signal from a loudspeaker of the automatic analysis device or is emitted in the form of a visual signal from a warning light of the automatic analysis device. This enables a user to engage as rapidly as possible to remedy the error, for example, by replacing the defective pipetting device.

The shutting down of the pipetting device ensures that no further reagent liquids or sample liquids are wasted.

In a further embodiment, the automatic analysis device comprises a controller, which is furthermore configured so that—if it is established that (b) the ascertained temperature difference is less than or equal to the predefined maximum temperature difference value—the following method steps are executed:

dispensing the aspirated volume of the reagent liquid from the pipetting needle into the reaction vessel, supplying the reaction vessel having the reaction mixture to a measurement unit, and measuring a physical property of the reaction mixture in the measurement unit.

The measurement unit of the automatic analysis device can be, for example, a photometer for extinction measurement, a nephelometer for the measurement of scattered light, a luminometer for the measurement of light emission (for example, fluorescence, phosphorescence, etc.), or a radiometer.

A "liquid to be analyzed" is primarily to be understood in the meaning of the present invention as human or animal bodily fluids, for example, blood, plasma, serum, urine, cerebrospinal fluid, amniotic fluid, etc., but also, for example, cell culture samples, vegetable liquids, water and wastewater samples, nutrients, or pharmaceuticals.

A "reagent liquid" is to be understood as a liquid which contains at least one substance, which is necessary for the qualitative or quantitative detection of an analyte. Depending on the type of the analyte and the detection reaction, for example, immunoreactive substances, for example, antibodies or antigens, or components of an enzyme reaction, for example, chromogenic substrates, come into consideration as detection substances.

BRIEF DESCRIPTION OF THE DRAWINGS

The invention will be explained hereafter on the basis of a drawing.

Identical parts are provided with the same reference signs in all figures.

DETAILED DESCRIPTION

Figure 1:
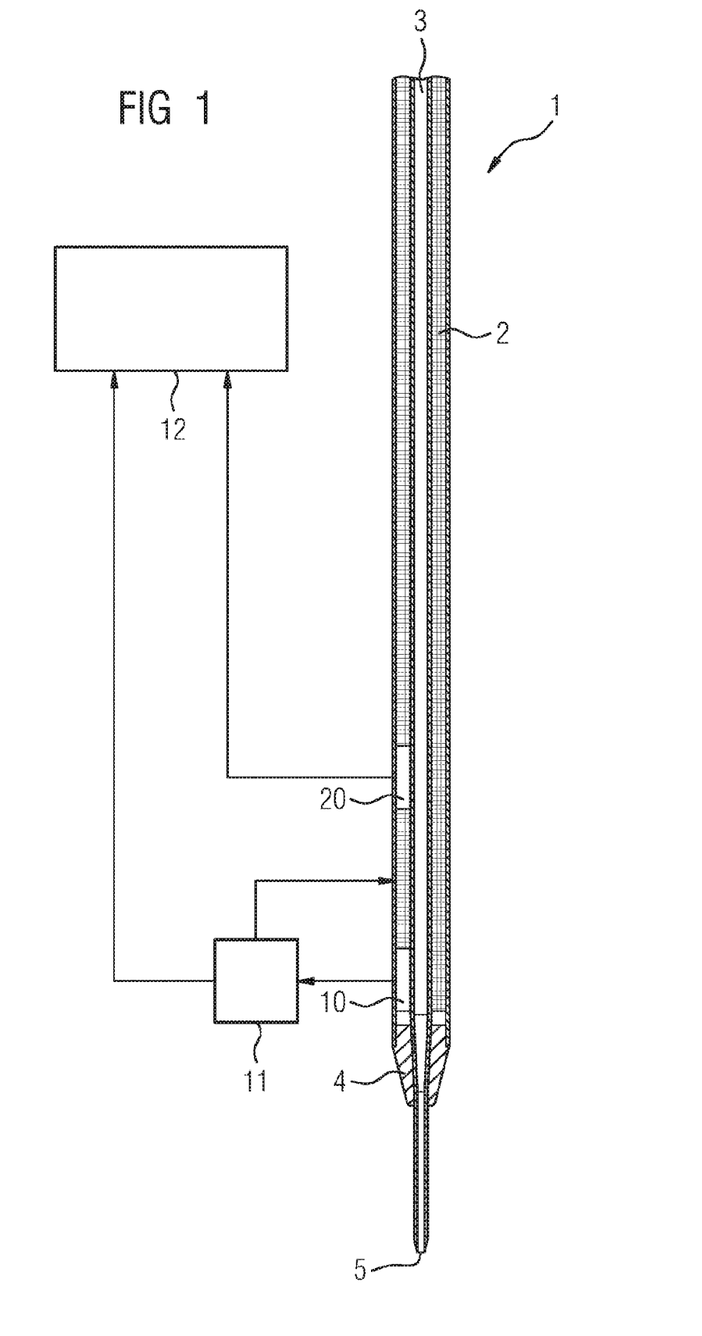
FIG. 1 shows a pipetting needle of a pipetting device according to the invention.

FIG. 1 is a schematic illustration of a heatable pipetting needle 1, which is part of a pipetting device (not shown in greater detail) of an automatic analysis device. The pipetting needle 1 consists of a cylindrical hollow needle made of stainless steel, which is wrapped with a heating wire 2. The pipetting needle 1 has an opening 3 at one end, which is connectable to an aspiration system, for example, to a cylinder and a piston movable therein. At the other end, the pipetting needle 1 has a conical tip 4 having an opening 5. The pipetting needle 1 has a first temperature sensor 10 and a second temperature sensor 20. The first temperature sensor 10, which is at a smaller distance from the needle tip 4 than the second temperature sensor 20, is directly connected to a controller 11, which can directly regulate the heat generation by the heating wire 2. The controller 11 is furthermore connected to a higher-order control unit 12, to which it can transmit the temperature, which is measured at a specific time by the temperature sensor 10. The second temperature sensor 20 is only used as a reference temperature sensor and therefore does not have a connection to a controller 11, but rather only a connection to the higher-order control unit 12, to which it can transmit the temperature measured by the temperature sensor 20 at a specific point in time.

Figure 2:
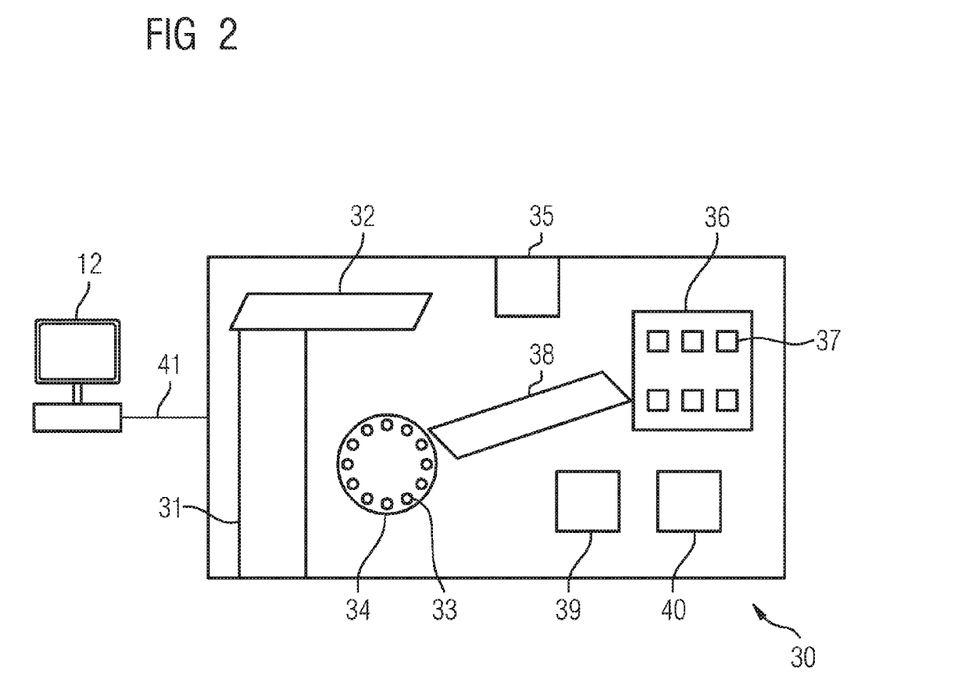
FIG. 2 shows an automatic analysis device according to the invention.

FIG. 2 is a schematic illustration of an automatic analysis device 30 having several components contained therein. In this case, only the most important components are shown in greatly simplified form, to explain the fundamental function of the automatic analysis device 30, without illustrating the individual parts of each component in detail in this case.

The automatic analysis device 30 is designed to carry out greatly varying analyses of blood or other bodily fluids completely automatically, without activities of a user being necessary for this purpose. Required interventions of a user are rather restricted to maintenance or repair and refilling work, for example, if cuvettes have to be refilled or reagent vessels have to be replaced.

The patient samples are supplied to the automatic analysis device 30 on carriages (not shown in greater detail) via a supply rail 31. Items of information with respect to the analyses to be carried out per sample can be transferred, for example, by means of barcodes attached to the sample vessels, which are read out in the automatic analysis device 30. Sample aliquots are removed from the sample vessels by means of a pipetting needle with the aid of a first pipetting device 32.

The sample aliquots are also supplied to cuvettes (not shown in greater detail), which are arranged in receptacle positions 33 of a rotatable incubation unit 34, which is temperature controlled to 37° C. The cuvettes are removed from a cuvette storage container 35. Reagent vessels 37 having various reagent liquids are stored in the reagent vessels storage container 36, which is cooled to approximately 8-10° C. Reagent liquid is removed by means of a heatable pipetting needle 1, as illustrated in FIG. 1, of a second pipetting device 38 according to the invention from a reagent vessel 37 and dispensed to provide a reaction mixture in a cuvette, which already contains a sample aliquot. If it is established during the check of the pipetting needle temperature, before dispensing of the reagent liquid, that the temperature lies in the predefined tolerance range, the cuvette is transported with the reaction mixture by a transfer arm (not shown) having a gripper from the incubation device 34 into a photometric measurement unit 39, where the extinction of the reaction mixture is measured. After completion of the measurement, the cuvette is disposed of in a waste container 40 for used cuvettes. However, if it is established during the check of the pipetting needle temperature, before dispensing of the reagent liquid, that the temperature lies outside the predefined tolerance range, the cuvette having the reaction mixture is transported by the transfer arm from the incubation unit 34 directly into the waste container 40.

The entire process is controlled by a control unit 12, for example, by a computer connected via a data line 41, assisted by a plurality of further electronic circuits and microprocessors (not shown in greater detail) within the automatic analysis device 30 and its components.

Figure 3:
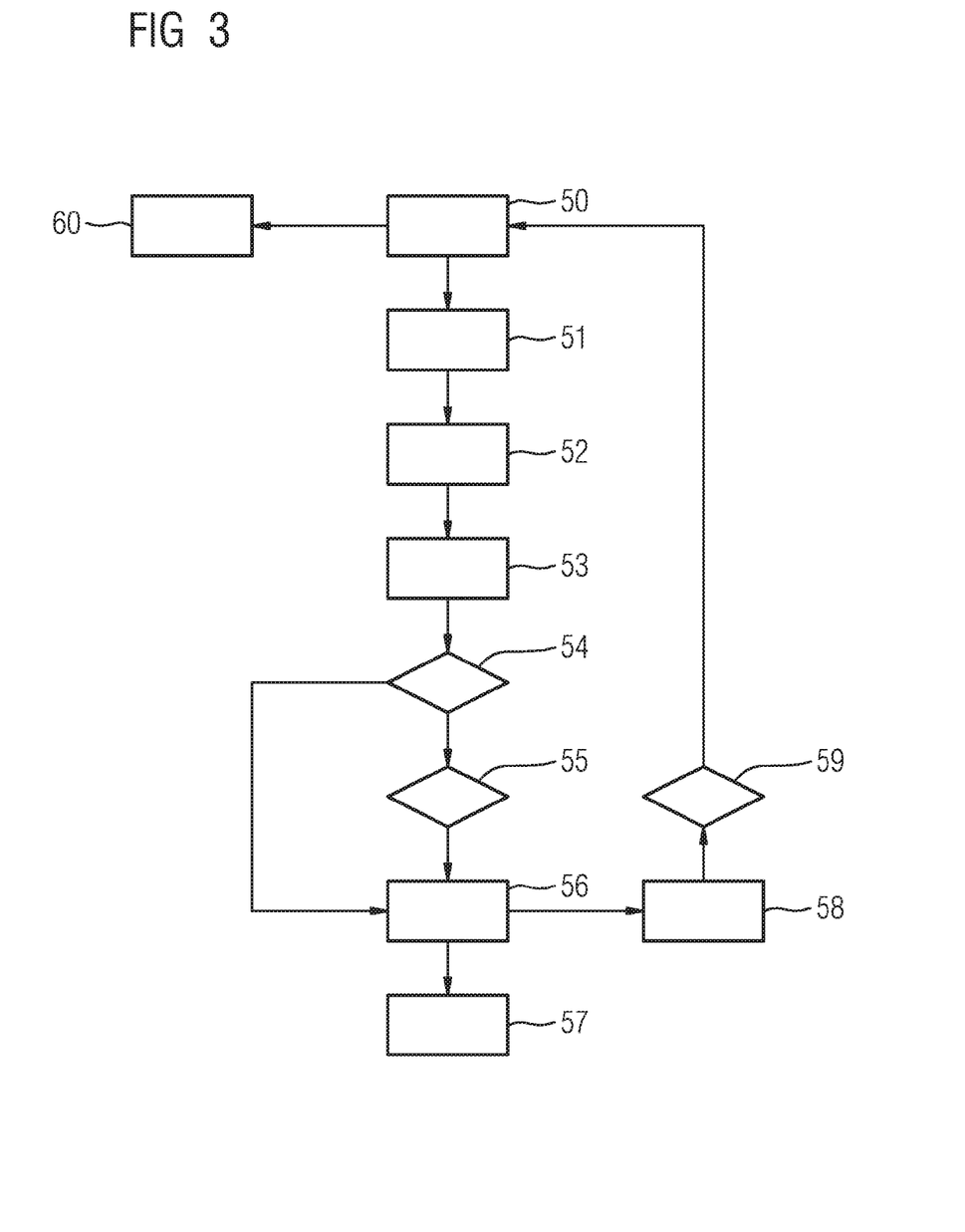
FIG. 3 shows a flow chart of a first variant of the method according to the invention for providing a reaction mixture.

FIG. 3 shows a flow chart of a method for providing a reaction mixture in the automatic analysis device 30 shown in FIG. 2, which, inter alia, comprises a pipetting device 38 having a pipetting needle 1 as shown in FIG. 1.

In step 50, an order for carrying out an analysis procedure, which comprises multiple steps, is issued by the central control unit 12. The pipetting device 38 contains specific instructions which carry out the steps necessary for this analysis procedure for the supply of the reagent liquid in a specific cuvette. In a first step 51 of the pipetting procedure, the pipetting device 38 is moved horizontally to the reagent vessel 37, which contains the required reagent liquid, the heated pipetting needle 1 is plunged into the cooled reagent liquid (approximately 8-10° C.), the requested volume is aspirated, and the pipetting needle 1 is removed from the reagent liquid. In a second step 52 of the pipetting procedure, the pipetting device 38 is moved horizontally to the incubation unit 34, which contains, in one of the receptacle positions 33, the cuvette, which is provided for receiving the reagent liquid and is already filled with sample liquid. During the movement of the pipetting device 38 from the removal location to the dispensing location, the reagent liquid is heated in the heated pipetting needle 1. In step 53 of the pipetting procedure, at the dispensing location, before dispensing of the reagent liquid, the temperature measured values of the temperature sensors 10, 20 of the pipetting needle 1 are acquired and transmitted to the higher-order control unit 12. In the control unit 12, in step 54, firstly the temperature measured by the first temperature sensor 10, which is close to the needle tip, is compared to a predefined minimum temperature and a predefined maximum temperature. If it is established in step 54 that the temperature measured by the temperature sensor 10 lies in the predefined tolerance range, in step 55, the absolute temperature difference between the temperature measured by the first temperature sensor 10 and the temperature measured by the second temperature sensor 20 is ascertained in the control unit 12 and compared to a predefined maximum temperature difference value. If it is established in step 55 that the absolute temperature difference is less than or equal to the predefined maximum temperature difference value, in step 56, the reagent liquid is then dispensed into the cuvette. In step 57, the cuvette having the reaction mixture is transported from the incubation unit 34 to the photometric measurement unit 39, where the extinction of the reaction mixture is measured. The extinction measured values are transmitted to the control unit 12, in which the analysis of the measurement results and the output of an analysis result are then performed.

However, if it is established in step 54 that the temperature measured by the temperature sensor 10 lies outside the predefined tolerance range, or if it is established in step 55 that the absolute temperature difference of the temperatures measured by the two temperature sensors is greater than the predefined maximum temperature difference value, after the dispensing of the reagent liquid into the cuvette in step 56, the sequence does not continue to step 57, but rather to step 58, in which the analysis procedure is terminated, in that the cuvette having the reaction mixture is transported from the incubation unit 34 to the waste container 40 and disposed of therein. In step 59, the information about the termination of the analysis procedure is transmitted to the control unit 12, whereupon the control unit 12 once again issues the order for carrying out the analysis procedure according to step 50.

For the case in which the same analysis procedure has to be terminated three times in succession, because the required criteria are not fulfilled in steps 54 or 55, in step 60, the pipetting device 38 is shut down by the central control unit 12, and an error message is generated for a user.

Figure 4:
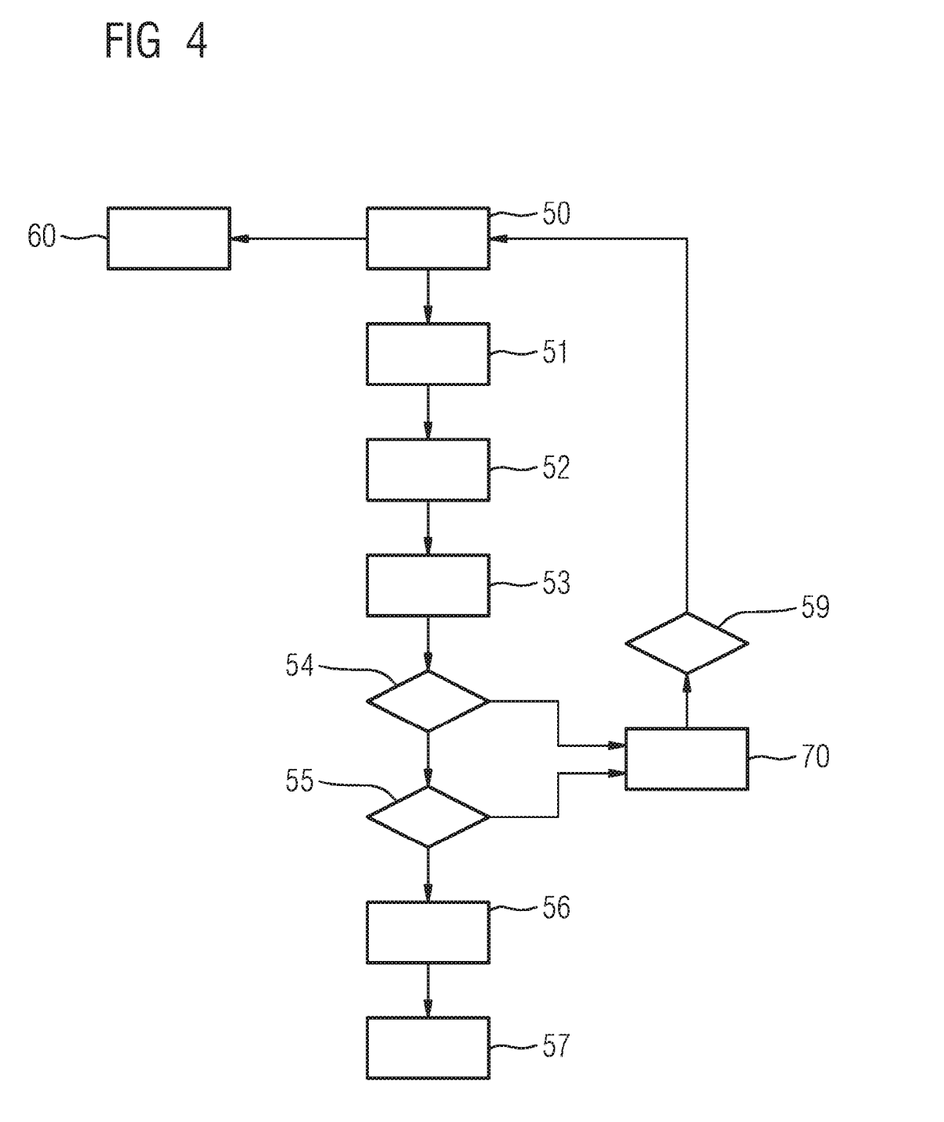
FIG. 4 shows a flow chart of a second variant of the method according to the invention for providing a reaction mixture.

FIG. 4 shows a flow chart of a somewhat modified method for providing a reaction mixture in the automatic analysis device 30 shown in FIG. 2, which comprises, inter alia, a pipetting device having a pipetting needle as shown in FIG. 1 and a washing station for pipetting needles.

Steps 50 to 57 are essentially identical to steps 50 to 57 of the method shown in FIG. 3. The difference is that if it is established in step 54 that the temperature measured by the temperature sensor 10 lies outside the predefined tolerance range, or if it is established in step 55 that the absolute temperature difference of the temperatures measured by the two temperature sensors is greater than the predefined maximum temperature difference value, no dispensing of the reagent liquid into the cuvette takes place in step 56, but rather the sequence transfers to step 70, in which the analysis procedure is terminated, in that the pipetting device 38 having the still aspirated reagent liquid in the pipetting needle 1 is moved to a washing station (not shown in FIG. 2) for pipetting needles and the reagent liquid is dispensed into the washing station and therefore disposed of.

This variant of the method has the advantage that the sample liquid is still available in the cuvette for a repetition of the analysis procedure.

Steps 59 and 60 are also identical to steps 59 and 60 of the method shown in FIG. 3.

LIST OF REFERENCE NUMERALS

1 pipetting needle
2 heating wire
3 opening
4 tip
5 opening
10 temperature sensor
11 controller
12 control unit 20 temperature sensor
30 analysis device
31 supply rail
32 pipetting device
33 receptacle position
34 incubation device
35 cuvette storage container
36 reagent vessel storage container
37 reagent vessel
38 pipetting device
39 measurement unit
40 waste container
41 data line
50-70 method steps

What is claimed is:

1. A pipetting device comprising:
a pipetting needle having a tip and having a first temperature sensor at a small distance from the tip of the pipetting needle and a second temperature sensor at a greater distance from the tip of the pipetting needle,
a heating device for heating the pipetting needle, and
a controller for regulating heat generation by the heating device,
wherein the first temperature sensor is connected to the controller and the second temperature sensor is not used by the controller to regulate heat generation by the heating device.

2. An automatic analysis device having at least one pipetting device as claimed in claim 1 and an automatically movable or pivotable transfer arm, wherein the at least one pipetting device is fastened on the automatically movable or pivotable transfer arm.

3. The automatic analysis device as claimed in claim 2 having multiple receptacle positions for receiving reagent vessels and having multiple receptacle positions for receiving reaction vessels and having at least one measurement unit for measuring a physical property of a reaction mixture, wherein the analysis device further comprises a control unit configured to control a method for providing a reaction mixture of a liquid to be analyzed and at least one reagent liquid in a reaction vessel, the method comprising:
heating the pipetting needle of the pipetting device;
aspirating a volume of a reagent liquid into the heated pipetting needle;
moving the pipetting needle to a desired location for dispensing of the aspirated volume of the reagent liquid into a reaction vessel; then
measuring a temperature using the first temperature sensor and a temperature using the second temperature sensor;
comparing the temperature measured by the first temperature sensor to a predefined minimum temperature and a predefined maximum temperature; and
establishing that the temperature measured by the first temperature sensor either:
exceeds the predefined maximum temperature, or
does not exceed the predefined maximum temperature and does not fall below the predefined minimum temperature, or
falls below the predefined minimum temperature,
wherein if it is established that the temperature measured by the first temperature sensor exceeds the predefined maximum temperature or falls below the predefined minimum temperature, the aspirated volume of the reagent liquid is dispensed from the pipetting needle and then disposed of.

4. The automatic analysis device as claimed in claim 3, wherein the control unit is further configured so that if it is established that the temperature measured by the first temperature sensor does not exceed the predefined maximum temperature and does not fall below the predefined minimum temperature, the method further comprises:
ascertaining the absolute temperature difference between the temperature measured by the first temperature sensor and the temperature measured by the second temperature sensor;
comparing the ascertained temperature difference to a predefined maximum temperature difference value; and
establishing that the ascertained temperature difference is either:
greater than the predefined maximum temperature difference value or
less than or equal to the predefined maximum temperature difference value,
wherein if it is established that the ascertained temperature difference is greater than the predefined maximum temperature difference value, the aspirated volume of the reagent liquid is dispensed from the pipetting needle and then disposed of.

5. The automatic analysis device as claimed in claim 4, wherein the control unit is further configured so that if it is established that the ascertained temperature difference is less than or equal to the predefined maximum temperature difference value, the method further comprises:
dispensing the aspirated volume of the reagent liquid from the pipetting needle into the reaction vessel,
supplying the reaction vessel having the reaction mixture to a measurement unit, and
measuring a physical property of the reaction mixture in the measurement unit.

* * * * *